US008891073B2

(12) United States Patent
Effenberger, Jr. et al.

(10) Patent No.: US 8,891,073 B2
(45) Date of Patent: Nov. 18, 2014

(54) APPARATUS, SYSTEM, AND METHOD FOR LASER-INDUCED BREAKDOWN SPECTROSCOPY

(75) Inventors: Andrew J. Effenberger, Jr., San Diego, CA (US); Jill R. Scott, Idaho Falls, ID (US); Timothy R. McJunkin, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 345 days.

(21) Appl. No.: 13/183,228

(22) Filed: Jul. 14, 2011

(65) Prior Publication Data
US 2013/0016349 A1 Jan. 17, 2013

(51) Int. Cl.
*G01N 21/00* (2006.01)
*G01J 3/30* (2006.01)
*G01B 9/02* (2006.01)
*G01J 3/443* (2006.01)
*G01J 3/26* (2006.01)
*G01N 21/71* (2006.01)
*G01J 3/18* (2006.01)

(52) U.S. Cl.
CPC .. *G01J 3/18* (2013.01); *G01J 3/443* (2013.01); *G01J 3/26* (2013.01); *G01N 21/718* (2013.01)
USPC .............................. 356/72; 356/318; 356/454

(58) Field of Classification Search
CPC .............. G01J 3/18; G01J 3/26; G01J 3/443; G01N 21/718
USPC ..................... 356/311, 313, 316, 318, 72, 454
See application file for complete search history.

(56) References Cited

U.S. PATENT DOCUMENTS

| 3,795,448 | A  | * | 3/1974 | Fletcher et al. | 356/28 |
| 3,853,404 | A  | * | 12/1974 | Barrett | 356/454 |
| 3,864,044 | A  | * | 2/1975 | Lyshkow | 356/436 |
| H001152 | H  | * | 3/1993 | Korendyke | 356/328 |
| 6,407,811 | B1 | * | 6/2002 | Snyder et al. | 356/316 |
| 6,741,345 | B2 | * | 5/2004 | Sabsabi et al. | 356/318 |
| 6,762,836 | B2 | * | 7/2004 | Benicewicz et al. | 356/318 |
| 7,233,643 | B2 |   | 6/2007 | Sipila et al. | |
| 7,394,537 | B1 |   | 7/2008 | Lindfors et al. | |

(Continued)

OTHER PUBLICATIONS

Bacon et al., "Atomic Spectrometry Update-Atomic Mass Spectrometry," Journal of Analytical Atomic Spectrometry, Oct. 1997, vol. 12 (407R-448R).

(Continued)

*Primary Examiner* — Michael A Lyons
*Assistant Examiner* — Shawn Decenzo
(74) *Attorney, Agent, or Firm* — TraskBritt

(57) ABSTRACT

In laser-induced breakdown spectroscopy (LIBS), an apparatus includes a pulsed laser configured to generate a pulsed laser signal toward a sample, a constructive interference object and an optical element, each located in a path of light from the sample. The constructive interference object is configured to generate constructive interference patterns of the light. The optical element is configured to disperse the light. A LIBS system includes a first and a second optical element, and a data acquisition module. The data acquisition module is configured to determine an isotope measurement based, at least in part, on light received by an image sensor from the first and second optical elements. A method for performing LIBS includes generating a pulsed laser on a sample to generate light from a plasma, generating constructive interference patterns of the light, and dispersing the light into a plurality of wavelengths.

26 Claims, 10 Drawing Sheets

(56) References Cited

U.S. PATENT DOCUMENTS

| | | | |
|---|---|---|---|
| 7,426,019 B2 | 9/2008 | Eklin | |
| 7,705,980 B2* | 4/2010 | Smous et al. | 356/301 |
| 2010/0158438 A1* | 6/2010 | Churikov et al. | 385/28 |

OTHER PUBLICATIONS

Baudelet et al., "Femtosecond time-resolved laser-induced breakdown spectroscopy for detection and identification of bacteria: A comparison to the nanosecond regine," Journal of Applied Physics, 99, 084701 (2006).

Becker et al., "Inductively coupled plasma mass spectrometry (ICP-MS) and laser ablation ICP-MS for isotope analysis of long-lived radionuclides," International Journal of Mass Spectrometry, 242 (2005) 183-195.

Becker et al., "Inorganic trace analysis by mass spectrometry," Spectrochimica Acta Part B (1998) 1475-1506.

Gondal et al., "On-line monitoring of remediation process of chromium polluted soil using LIBS," Journal of Hazardous Materials, 163 (2009) 1265-1271.

Harmon et al., "LIBS analysis of geomaterials: Geochemical fingerprinting for the rapid analysis and discrimination of minerals," Applied Geochemistry, 24 (2009) 1125-1141.

Hussain et al., "Monitoring and assessment of toxic metals in Gulf War oil spill contaminated soil using laser-induced breakdown spectroscopy," Environ Monit Assess (2008) 136:391-399.

Kim et al., "Spectral Fingerprints of Bacterial Strains by Laser-Induced Breakdown Spectroscopy," J. Phys. Chem. B, 2004, 108, 5477-5482.

Kutschera, Walter, "Progress in isotope analysis at ultra-trace level by AMS," International Journal of Mass Spectrometry 242 (2005) 145-160.

Lopez-Moreno et al., "Test of a stand-off laser-induced breakdown spectroscopy sensor for the detection of explosive residues on solid surfaces," J. Anal. At. Spectrom., 2006, 21, 55-60.

Lu et al., "Laser-based methods for ultrasensitive trace-isotope analyses," Review of Scientific Instruments, vol. 74, No. 3, Mar. 2003.

Muzikar et al., "Accelerator mass spectrometry in geologic research," Geological Society of America Bulletin, 2003; 115; 643-654.

Osticioli et al., "An Optimization of Parameters for Application of a Laser-Induced Breakdown Spectroscopy Microprobe for the Analysis of Works of Art," Applied Spectroscopy, vol. 62, No. 11, 2008.

Pietsch, et al., "Isotope ratio determination of uranium by optical emission spectroscopy on a laser-produced plasma—basic investigations and analytical results," Spectrochimica Acta Part B, 53 (1998) 751-761.

Rodriguez-Celis et al., "Laser induced breakdown spectroscopy as a tool for discrimination of glass for forensic applications," Anal. Bioanal. Chem (2008) 391:1961-1968.

Smith et al., "Pu-239/Pu-240 isotope ratios determined using high resolution," Spectrochimica Acta Part B, 57 (2002) 929-937.

Suliyanti et al., "Preliminary analysis of C and H in a "Sangiran" fossil using laser-induced plasma at reduced pressure," Journal of Applied Physics, 98, 093307 (2005).

Vanhaecke et al., "Overcoming spectral overlap in isotopic analysis via single- and multi-collector ICP-mass spectrometry," Anal Bioanal Chem (2004) 378:232-240.

Wasowicz et al. "Hyperfine structure and isotope shifts in 461.9 nm forbidden line of Pb I," Optica Applicata, vol. 36, No. 4 (2006) 529-533.

Wasowicz et al., "Hyperfine Structure Study of Several Lines of 207Pb I," Physica Scripta. vol. 71, 274-276, 2005.

Wasowicz et al., "Hyperfine Structure Study of Several Lines of 207Pb I—Part II," Physica Scripta. vol. 72, 200-202, 2005.

Wendt et al., "Recent developments in isotope ratio measurements by resonance ionization mass spectrometry," International Journal of Mass Spectrometry, 242 (2005) 161-168.

Whitehouse et al., "Remote material analysis of nuclear power station steam generator tubes by laser-induced breakdown spectroscopy," Spectrochimica Acta Part B, 56 (2001) 821-830.

Economou, T.E., "Application of radioactive sources in analytical instruments for planetary exploration," Appl. Radiat. Isot. 68 (2010) 542-545.

Effenberger et al., "Effect of Atmospheric Conditions on LIBS Spectra," Sensors 10 (2010) 4907-4925.

Harkins et al., "Lead Isotope Constraints on the Origin of Nonsulfide Zinc and Sulfide Zinc-Lead Deposits in the Flinders Ranges, South Australia," Econ. Geol. 103 (2008) 353-364.

Hosono et al., "Historical record of heavy metal pollution deduced by lead isotope ratios in core sediments from the Osaka Bay, Japan," J. Geochem. Explor 107 (2010) 1-8.

King et al., "Rubidium isotope measurements in solid samples by laser ablation-laser atomic absorption spectroscopy," Spectrochimica Acta Part B-Atomic Spectroscopy 54 (1999) 1771-1781.

Kotarba, M., "Isotopic geochemistry and habitat of the natural gases from the Upper Carboniferous Zacler coal-bearing formation in the Nowa Ruda coal district (lower Silesia, Poland)" Org. Geochem. 16 (1990) 549-560.

Liu et al., "Diode laser absorption measurement of uranium isotope ratios in solid samples using laser ablation," Spectrochimica Acta Part B-Atomic Spectroscopy 57 (2002) 1611-1623.

Mikhalsky, et al., "New Sm-Nd, Rb-Sr, U-Pb and Hf isotope systematic for the southern Prince Charles Mountains (East Antarctica) and its tectonic implications," Precambrian Res. 182 (2010) 101-123.

Ono, S., "Multiple-Sulphur Isotope Biosignatures," Space Sci. Rev. 135 (2008) 203-220.

Quentmeier et al. "Measurement of uranium isotope ratios in solid samples using laser ablation and diode laser-atomic absorption spectrometry," Spectrochimica Acta Part B-Atomic Spectroscopy 56 (2001) 45-55.

Reguir et al., "Trace-element study and uranium-lead dating of perovskite from the Afrikanda plutonic complex, Kola Peninsula (Russia) using LA-ICP-MS," Mineral. Petrol. 100 (2010) 95-103.

Resano et al., "Laser ablation single-collector inductively coupled plasma mass spectrometry for lead isotopic analysis to investigate evolution of the Bilbilis mint," Anal. Chim. Acta 677 (2010) 55-63.

Shen et al., "Detection of uranium in solids by using laser-induced breakdown spectroscopy combined with laser-induced fluorescence," Applied Optics 47 (2008) 1810-1815.

Smith et al., "Measurement of uranium isotope ratios in solid samples using laser ablation and diode laser-excited atomic fluorescence spectrometry," Spectrochimica Acta Part B-Atomic Spectroscopy 54 (1999) 943-958.

Tsygankov et al., "Sequence of magnatic events in the Late Paleozoic of Transbaikalia, Russia (U-Pb isotope data)," Russ. Geol. Geophys. 51 (2010) 972-994.

Weber et al., "U-Pb and Lu-Hf isotope systematic of lower crust from central-southern Mexico—Geodynamic significance of Oaxaquia in a Rodinia Realm," Precambrian Res. 182 (2010) 149-162.

Yang et al., "Zircon U-Pb geochronology, Hf isotopic composition and geological implications of the rhyodacite and rhyodacitic porphyry in the Xiangshan uranium ore field, Jiangxi Province, China," Sci. China-Earth Sci. 53 (Oct. 2010) 1411-1426.

Doucet et al., "Determination of Isotope Ratios Using Laser-Induced Breakdown Spectroscopy in Ambient Air at Atmospheric Pressure for Nuclear Forensics," J. Anal. At. Spectrom., 26, 536-541 (2011).

Effenberger et al., "Effect of Atmosphere on Collinear Double-Pulse Laser-Induced Breakdown Spectroscopy," Anal. Bioanal. Chem., 400, 3217-3227 (2011).

* cited by examiner

APPARATUS, SYSTEM, AND METHOD FOR LASER-INDUCED BREAKDOWN SPECTROSCOPY

GOVERNMENT RIGHTS

This invention was made with government support under Contract Number DE-AC07-05ID14517 awarded by the United States Department of Energy. The government has certain rights in the invention.

TECHNICAL FIELD

Embodiments of the present disclosure relate generally to laser-induced breakdown spectroscopy (LIBS) and, more specifically, to an apparatus, a system, and a method relating to operation of optical detection components of a LIBS system.

BACKGROUND

Various methods are employed for determining the material constitution of a sample, which may include obtaining isotopic measurements of the sample. For example, isotopic measurements of the sample may be acquired by using mass spectrometers, which may operate through techniques such as accelerator mass spectrometry (AMS), magnetic sector mass spectrometry (MSMS), resonance ionization mass spectrometry (RIMS), and which may use a variety of ionization sources (e.g., thermal ionization (TI), inductively couple plasma (ICP), etc.) in order to analyze positive or negative ions from the sample. Each of these mass spectrometry techniques generally requires extensive sample preparation or additional instrumentation (e.g., a furnace for RIMS) to enable sample analysis. In addition, the instruments used for mass spectrometers may be relatively large and expensive.

Other methods for acquiring the isotope measurements and isotope ratio detection of the sample include optical methods. Examples of such optical methods include laser ablation-laser induced fluorescence and laser ablation-laser absorption. Such optical methods generally require generating at least two laser beams (i.e., a first laser beam for sampling and a second laser beam for analysis and detection).

Laser-induced breakdown spectroscopy (LIBS) is another optical method for performing isotopic measurements. LIBS includes generating a single laser pulse for both sampling and detection, although multiple laser pulse techniques, such as collinear double-pulsed LIBS, are also employed. The laser pulse may be focused toward a sample, such as onto a surface of a sample (e.g., solid or liquid) or into a sample (e.g., liquid or gas). The laser pulse exhibits a high enough power density to transform at least a part of the sample into a state of a plasma. Optical emissions from the plasma plume are collected with light collection optics, and the spectral distribution (i.e., intensity as a function of wavelength) of the collected optical emissions is analyzed with a spectrometer by collecting optical emissions and generating electronic information describing the spectral distribution of the collected optical emissions. Because atomic and molecular constituents of sample materials exhibit a characteristic optical emission spectrum, the information generated by the spectrometer forms a "fingerprint" of the sample material, revealing the constituents of that part of the sample onto which the laser beam was focused. LIBS can also measure the isotopic line shift, which may be used to determine the isotope ratio of elements. An advantage of using LIBS over laser ablation-laser induced fluorescence or laser ablation-laser absorption for isotope measurements is that LIBS can be employed to generate a single laser pulse for both sampling and detection, which may simplify the instrument design.

While the use of LIBS may overcome the issue related to sample preparation of the mass spectrometry techniques, conventional LIBS systems are still relatively large and expensive because of the optical detection instrumentation needed to acquire sufficient resolution. For example, at least some isotopic line shift measurements may require a high-resolution spectrometer with resolution better than about 10 pm Full Width at Half Maximum (FWHM). Most conventional spectrometers, however, have a resolution of approximately 100 pm FWHM, which may be insufficient for many isotope measurements. Some conventional LIBS systems may employ a Czerny-Turner spectrometer that includes a double pass grating having a 2 m focal length that is used to perform relatively high-resolution isotope measurements. An alternative to a 2 m focal length Czerny-Turner spectrometer may be an Echelle spectrometer, which may also be relatively large and expensive.

DETAILED DESCRIPTION

Figure 1:
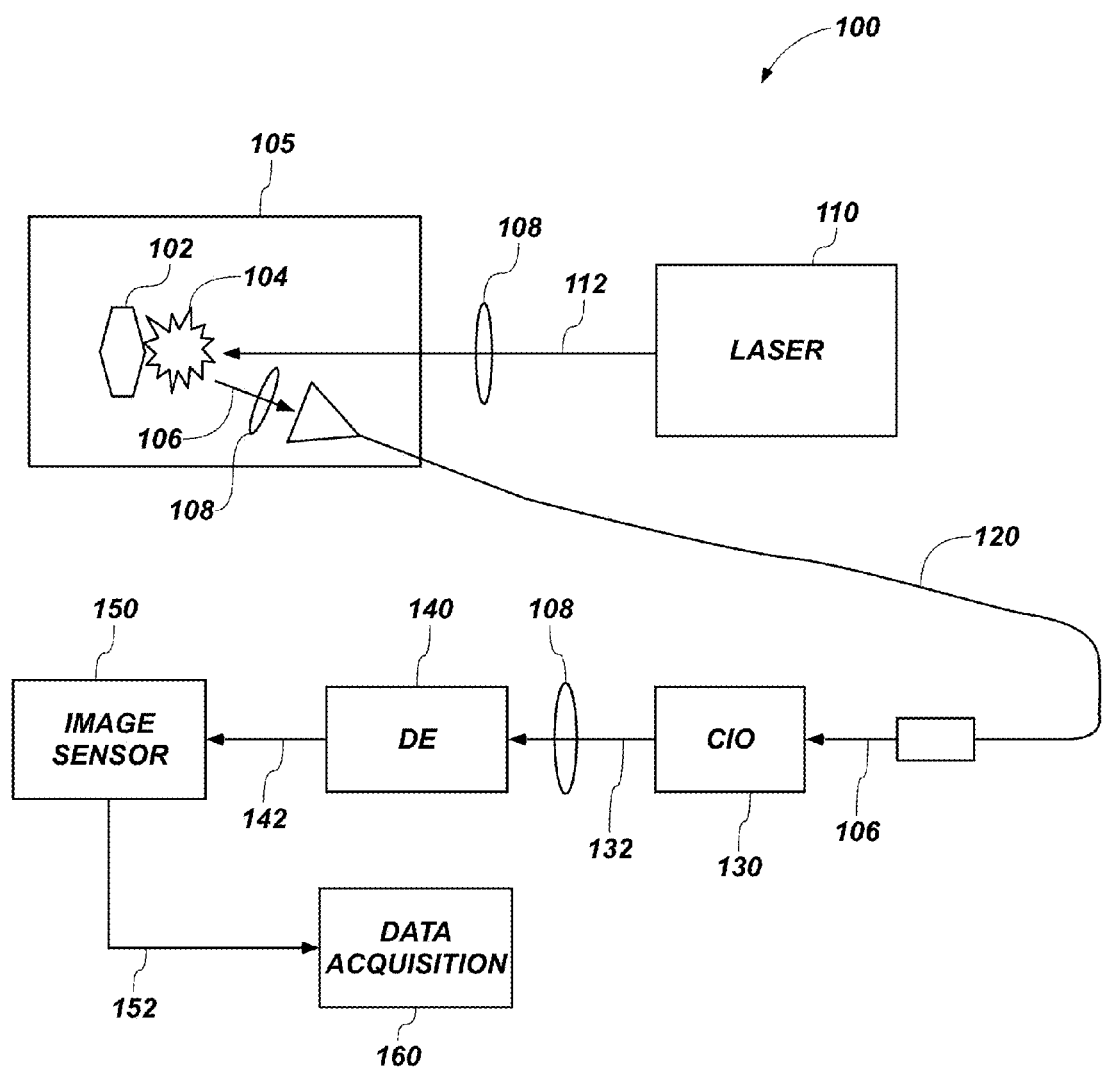
FIG. 1 is a schematic block diagram of a LIBS system according to an embodiment of the present disclosure.

In the following detailed description, reference is made to the accompanying drawings which form a part hereof and, in which is shown by way of illustration, specific embodiments in which the invention may be practiced. These embodiments of the present disclosure are described in sufficient detail to enable those of ordinary skill in the art to practice the invention, and it is to be understood that other embodiments may be utilized, and that structural, logical, and electrical changes may be made within the scope of the disclosure.

The various illustrative logical blocks, modules, and circuits described in connection with the embodiments disclosed herein may be implemented or performed with a processor such as a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It should be understood that any reference to an element (e.g., element, object, etc.) herein using a designation such as "first," "second," and so forth does not limit the quantity or order of those elements, unless such limitation is explicitly stated. Rather, these designations may be used herein as a convenient method of distinguishing between two or more elements or instances of an element. A reference to first and second elements does not mean that only two elements may be employed there or that the first element must precede the second element in some manner. Also, unless stated otherwise a set of elements may comprise one or more elements.

In this description, specific implementations shown and described are only examples and should not be construed as the only way to implement the present invention unless specified otherwise herein. It will be readily apparent to one of ordinary skill in the art that the various embodiments of the present invention may be practiced by numerous other partitioning solutions. Referring in general to the following description and accompanying drawings, various embodiments of the present disclosure are illustrated to show its structure and method of operation. Common elements of the illustrated embodiments may be designated with like reference numerals. It should be understood that the figures presented are not meant to be illustrative of actual views of any particular portion of the actual structure or method, but are merely idealized representations employed to more clearly and fully depict the present invention defined by the claims below.

FIG. 1 is a schematic of a LIBS system 100 according to an embodiment of the present disclosure. The LIBS system 100 includes a chamber 105, a laser 110, a fiber optic cable 120, a constructive interference object (CIO) 130, a dispersion element (DE) 140, an image sensor 150, and a data acquisition module 160. The LIBS system 100 may further include one or more focus lenses 108 positioned at various locations in the path of a laser pulse 112 generated by the laser 110, or in the path of light 106 generated from a sample 102 or at other locations in order to focus light for further processing.

The constructive interference object 130 may be an etalon, an interferometer, or other optical device that is configured to generate constructive interference patterns responsive to the light 106. Examples of specific types of etalons and interferometers include Fabry-Perot, Gires-Tournois, a Lummer-Gehrcke, and Fizeau. An example of a Fabry-Perot etalon may be available from SLS Optics Limited of Isle of Man, British Isles. Fabry-Perot etalons conventionally have been used in optical spectrometry, usually as filters for selecting wavelength ranges or to filter and "clean up" a laser signal. In embodiments of the present disclosure, the constructive interference object 130 generate rings 132 of light, which will be discussed more fully with respect to FIGS. 8 through 12. As used herein, the term "rings" of light means a light pattern (i.e., an image) in which photons are dispersed into substantially concentric rings, with the radius of each ring depending on the wavelength of the photons.

The dispersion element 140 may be configured to generate a dispersed spectrum in response to the light 106. For example, the dispersion element 140 may be a Czerny-Turner spectrometer, which may employ a grating (not shown; see FIG. 2). An example of a Czerny-Turner spectrometer may be a SpectraPro 500i Czerny-Turner spectrometer available from Acton Research Corporation, of Acton, Mass. In some embodiments, the dispersion element 140 may be a prism, a bent optical fiber, or other dispersion elements configured to disperse and filter wavelengths of light.

The image sensor 150 may be a charge-coupled device (CCD) camera, a complimentary metal-oxide-semiconductor (CMOS) sensor, or another electronic-based imaging device that converts an optical image to an electrical signal. As a non-limiting example, the image sensor 150 may be the PI-MAX 512×512 pixel ICCD camera available from Princeton Instruments of Trenton, N.J. Such an image sensor 150 may have an effective pixel size of 24 μm.

The data acquisition module 160 may include hardware (e.g., a processor) that receives the data signal 152 from the image sensor 150, and software that includes control logic configured to analyze or otherwise process the data signal 152. For example, the data acquisition module 160 may be the Winspec/32 module available from Princeton Instruments of Trenton, N.J. As an example, the software and the image sensor 150 may be operated in image mode, and the data may be exported in ASCII. Data processing may be performed in data processing and software modules (e.g., MATLAB®). Data processing may be performed in custom software, firmware, or computational hardware, such as an FPGA, for high throughput or compact integration.

The laser 110 may be configured to generate a laser pulse 112 having a desired wavelength, with the laser pulse 112 being generated according to a desired operating frequency. For example, the laser 110 may generate a 1064 nm laser pulse 112 operating at 10 Hz with an energy of 25 mJ. The irradiance of the laser pulse 112 may be approximately $10^{11}$ W/cm2. For example, the laser 110 may be Nd:YAG laser, such as the Continuum Precision II model available from CONTINUUM® of Santa Clara, Calif. Other pulsed laser characteristics, including different wavelengths and operating frequencies are contemplated.

In operation, the sample 102 may be placed within the chamber 105 (e.g., atmospheric chamber, vacuum chamber). In some embodiments, the sample 102 may be positioned in the open air as long as the laser pulse 112 can be sufficiently focused on or in the sample 102. The sample 102 may be a solid, a gas, or a liquid sample. As discussed above, LIBS is a real-time spectroscopic technique capable of providing rich atomic information regarding the constituents of the sample 102, and may be performed with little, to no, preparation of the sample 102. As a result, LIBS may be substantially non-destructive to the sample 102.

The laser 110 generates a laser pulse 112. The laser pulse 112 may be transmitted from the laser 110 through a focus lens 108, through a window in the chamber 105 and onto the sample 102. In some embodiments the focus lens and the window in the chamber may be one and the same. If the laser pulse 112 interacts with the sample 102, a plasma 104 may be created that generates the light 106. The light 106 generated from the plasma 104 may be transmitted to the constructive interference object 130 and the dispersion element 140. For example, the light 106 may be focused onto the fiber optic cable 120 for transmission (e.g., routing) to the constructive interference object 130. While other methods of light transmission may be used, fiber optics may be particularly useful for transmission in harsh environments and over long ranges.

The constructive interference object 130 may receive the light 106, and be configured to transmit the light 106 as a relatively complex set of rings 132 of light that are created through interfaces of the constructive interference object 130. The dispersion element 140 may be configured to filter out certain wavelengths of light that would otherwise create an extraordinarily complex set of rings of light. As a result, filtered rings 142 of light may be transmitted from the dispersion element 140 as the final image of the light 106 received by the image sensor 150. The image sensor 150 may be configured to receive and detect the filtered rings 142 of light and responsively transmit a data signal 152 to the data acquisition module 160 for further processing and analysis of the data signal 152.

Figure 2:
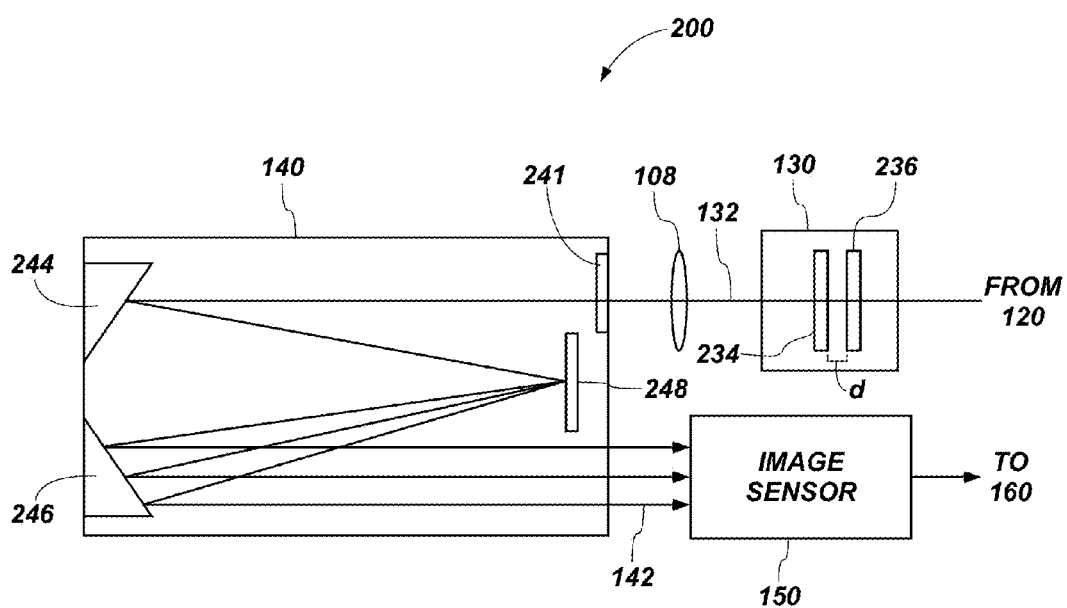
FIG. 2 depicts an optical system of a LIBS system according to an embodiment of the present disclosure.
Figure 3:
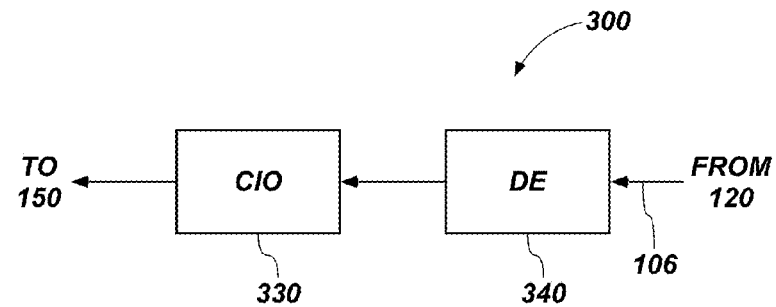
FIGS. 3 through 6 depict optical systems of a LIBS system according to various embodiments of the present disclosure.
Figure 4:
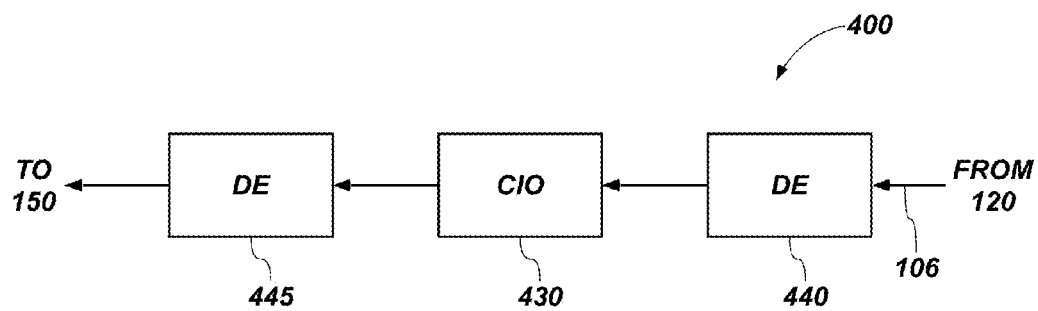
Figure 5:
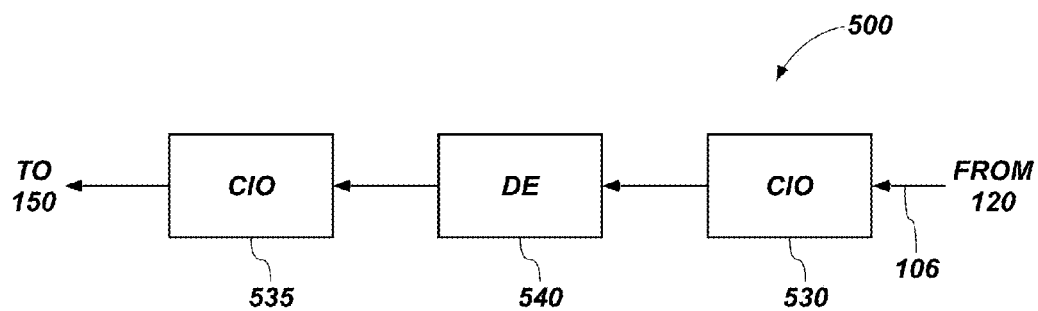
Figure 6:
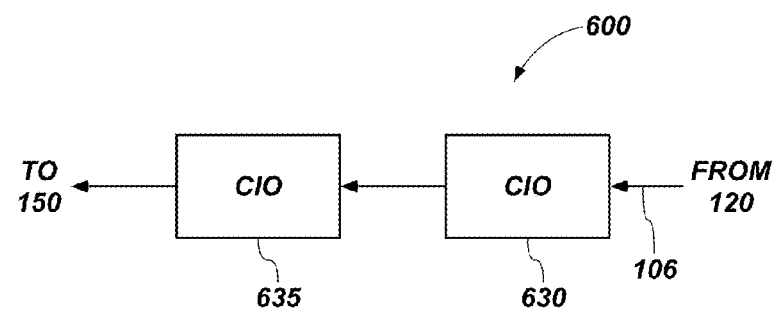

FIG. 2 depicts an optical system 200 of a LIBS system according to an embodiment of the present disclosure. The optical system 200 includes the constructive interference object 130 and the dispersion element 140 positioned between the fiber optic cable 120 and the image sensor 150 such that light 106 from the fiber optic cable 120 passes through the optical system 200 to the image sensor 150. As previously described above with respect to FIG. 1, the constructive interference object 130 may be configured as a Fabry-Perot etalon, and the dispersion element 140 may be a Czerny-Turner spectrometer.

Referring specifically to FIG. 2, the dispersion element 140 may include a plurality of reflective plates 244, 246 (e.g., mirrors) and a diffraction grating 248. As an example, the diffraction grating 248 of the dispersion element 140 may include approximately 1800 grooves per mm (g/mm). The constructive interference object 130 may include the plurality of reflective plates 234, 236 (e.g., mirrors) being separated by a gap of some distance (d). The gap may be maintained by a material (e.g., spacers) between the reflective plates 234, 236. In some embodiments that gap may be an air gap between the reflective plates 234, 236.

Attributes of the constructive interference object 130 that may contribute to achieving a desired resolution are the free spectral range (FSR) and effective finesse (Feff). The FSR is the wavelength separation between adjacent transmission peaks of the reflected light between the reflective plates 234, 236. The FSR may be determined, at least in part, by the thickness of the gap (e.g., spacers, air gap, etc.) between the reflective plates 234, 236. The Feff is a function of the reflectivity of the reflective plates 234, 236. The constructive interference object 130 may further include a coating configured for the reflection of certain wavelengths of light, which may further affect the Feff. For example, the reflective plates 234, 236 of a Fabry-Perot etalon (i.e., constructive interference object 130) may be conventionally coated with silver or aluminum. In some embodiments, a dielectric film may disposed over the reflective plates 234, 236, which may reduce absorption at approximately 313 nm, which is near the wavelength of the mercury (Hg) emission detected in the examples provided in this disclosure. As a result, using a dielectric film coating may cause the Fabry-Perot etalon to operate within narrow spectral region compared with a silver or aluminum coating. Some embodiments may include a broadband dielectric coating, which may improve measurements throughout at least a portion of the visible region (e.g., approximately 400 nm to 600 nm). Such dielectric coatings are known in the optical industry and may be combined to produce various reflective and transmissive ranges throughout the ultraviolet, visible, and infrared regions as needed for a specific application.

The ratio of the FSR and the Feff may provide an estimate of the FWHM of the rings 132 of light of the constructive interference object 130. For example, the FSR of the constructive interference object 130 may be approximately 0.111 nm, the Feff may be approximately 20.29, and the FWHM may be approximately 5.3 pm. As a result, the FWHM may be improved by increasing the reflectivity of the mirrors (i.e., increasing the Feff) or increasing the spacing between the mirrors (i.e., decreasing the FSR). Therefore, altering one or more of these variables may be performed to achieve appropriate parameters for the different types of optics desired for a particular use.

In operation, the rings 132 of light transmitted from the constructive interference object 130 may be focused through a slit 241 (e.g., a 500 μm) of the dispersion element 140. After a reflection on a mirror 244, the light may be dispersed by the diffraction grating 248, resulting in filtered rings 142 of light arranged in vertical strips (i.e., columns). The constructive interference object 130 may be aligned with the dispersion element 140 to allow a portion of the top part of the rings 132 of light to be imaged. The top part of the rings 132 of light may be a relatively flat portion of the rings 132 of light. If the width of the slit 241 is increased, a relatively greater portion of the rings 132 of light may be projected onto the image sensor 150, which may result in some overlap in the columns of the rings projected onto the image sensor 150.

The combination of the constructive interference object 130 (e.g., Fabry-Perot etalon) and the dispersion element 140 (e.g., Czerny-Turner spectrometer) may allow for a shorter focal length, which may enable the use of a smaller optical configuration. For example, as conventional LIBS systems may require a Czerny-Turner spectrometer having a relatively long focal length (e.g., 2 m) in order to achieve an appropriate high resolution (e.g., approximately 10 pm FWHM or less), embodiments of the present disclosure may achieve a similarly high resolution (e.g., 10 pm FWHM or less) with a Czerny-Turner spectrometer as the dispersion element 140 having a substantially reduced focal length (e.g., 0.5 m). Therefore, the size and cost of the LIBS system 100 may be substantially reduced in comparison to conventional LIBS systems.

FIGS. 3 through 6 depict optical systems 300 through 600 of a LIBS system according to various embodiments of the present disclosure. While the embodiments of FIGS. 1 and 2 illustrate light 106 travelling through a constructive interference object 130 followed by a dispersion element 140, other arrangements of optical elements are contemplated. For example, an optical system 300 of FIG. 3 may have a dispersion element 340 followed by a constructive interference element 330. Optical system 400 of FIG. 4 may have a first dispersion element 440 followed by a constructive interference object 430 and a second dispersion element 445 before the final image of the light 106 is transmitted to the image sensor 150. Optical system 500 of FIG. 5 may include a first constructive interference object 530 followed by a dispersion element 540 and a second constructive interference object 535 before the final image of the light 106 is transmitted to the image sensor 150. Optical system 600 of FIG. 6 may include a first constructive interference object 630 followed by a second constructive interference object 635. As noted above, these examples do not limit the quantity or order of those elements or objects.

For the optical systems 300 through 600 of FIGS. 3 through 6, when introducing additional optical elements and configurations, the final image of light 106 projected onto the image sensor 150 can become relatively complex. As a result, the analysis of the data acquisition module 160 used to interpret and translate the final image of light 106 into a useful spectrum may be relatively complex in comparison to that of FIG.

1. Other optical arrangements are contemplated as embodiments of the present disclosure that can produce even more complex images, but which may require even more elaborate analysis methods in order to translate the final images of light 106 into useful spectra. Even with the CIO-DE configuration for the optical systems of FIGS. 1 and 2, the final image of light 106 that is received by the image sensor 150 may be analyzed by what may be considered to be an elaborate analysis method performed by the data acquisition module 160.

Figure 7:
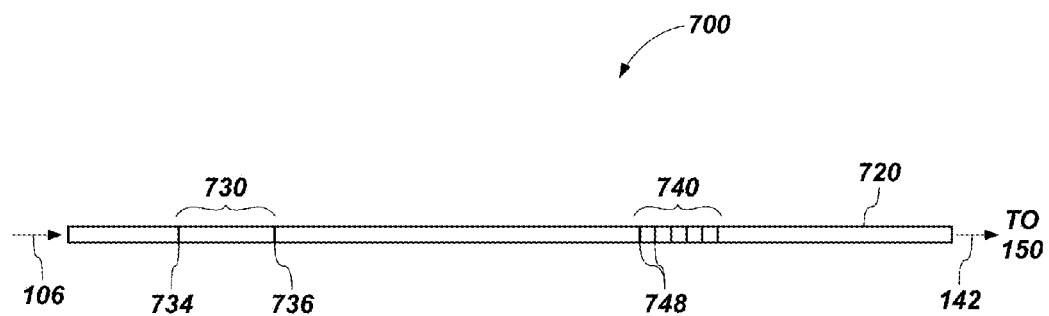
FIG. 7 depicts an optical system of a LIBS system according to another embodiment of the present disclosure.

FIG. 7 is an optical system 700 of a LIBS system according to another embodiment of the present disclosure. The optical system 700 includes a fiber optic cable 720 that includes a constructive interference object 730 and a dispersion element 740. In other words, at least a portion of, or all, of the optical elements of the optical system 700 may be constructed and integrated within the optical fiber of the fiber optic cable 720.

As an example, the constructive interference object 730 may constructed as a Fabry-Perot etalon arrangement having a pair of reflective elements 734, 736 formed within the optical fiber of the fiber optic cable 720. The dispersion element 740 may be constructed as a diffraction grating formed within the optical fiber of the fiber optic cable 720, such as being inscribed with Bragg gratings 748. In some embodiments, the optical fiber of the fiber optic cable 720 may be bent such that the light 106 may be dispersed through the side of the optical fiber in order to create the desired effects of the constructive interference object 730 and the dispersion element 740. Of course, different optical arrangements are contemplated for the optical system 700, in addition to the constructive interference object 730 and the dispersion element 740 shown in FIG. 7. For example, optical arrangements, such as those described with respect to FIGS. 3 through 6 may be formed within the fiber optic cable 720. Incorporating the constructive interference object 730 and the dispersion element 740 within the fiber optic cable 730 may enable further miniaturization of the optical system 700 (and therefore also the LIBS system 100 (FIG. 1)) relative to optical systems in which one or more of the constructive interference objects or dispersion elements are not integrated with a fiber optic cable.

Figure 8:
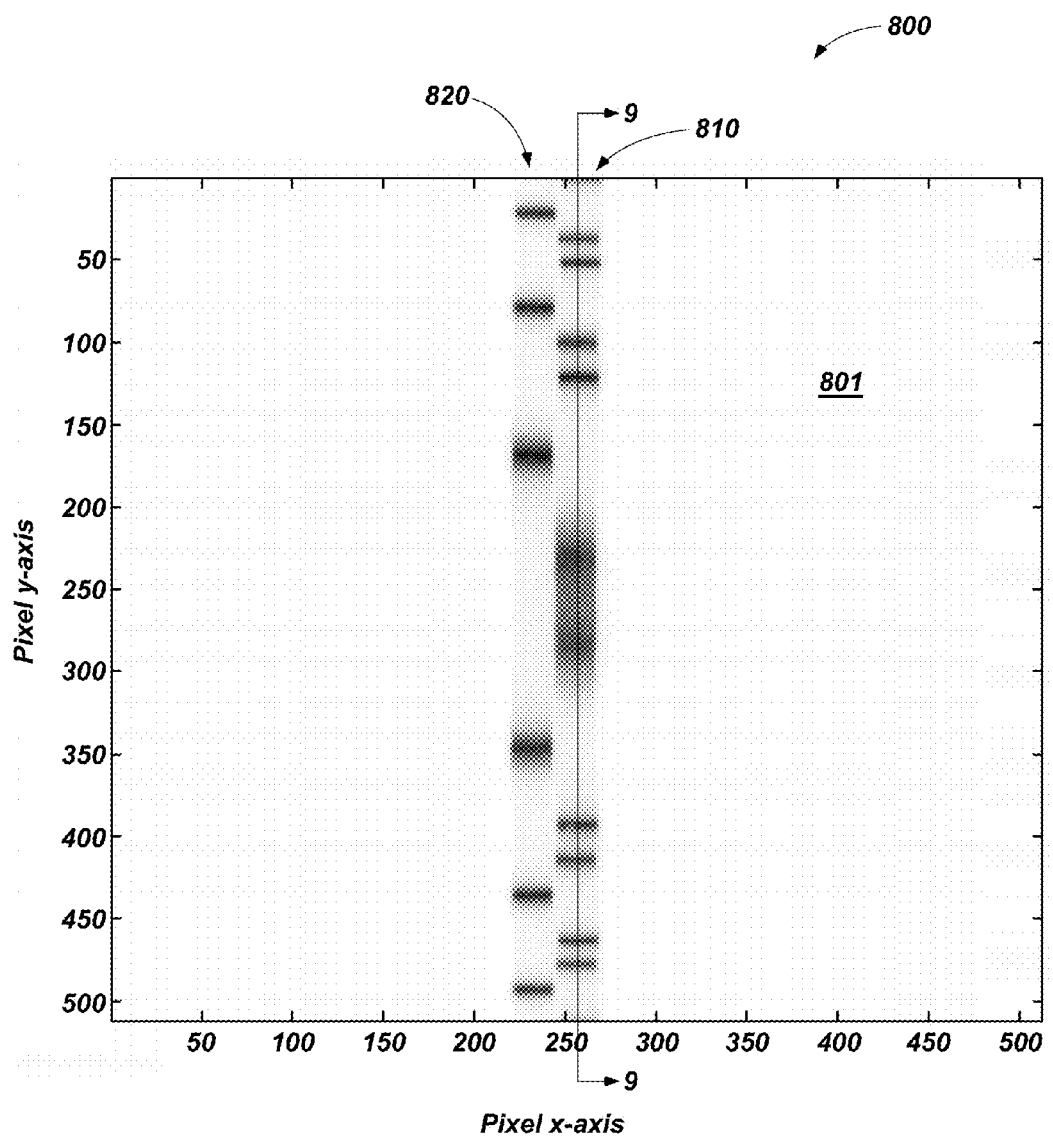
FIGS. 8 through 10 show analysis of the final images generated by the LIBS system of FIG. 1 acquired from a continuous light source.
Figure 9:
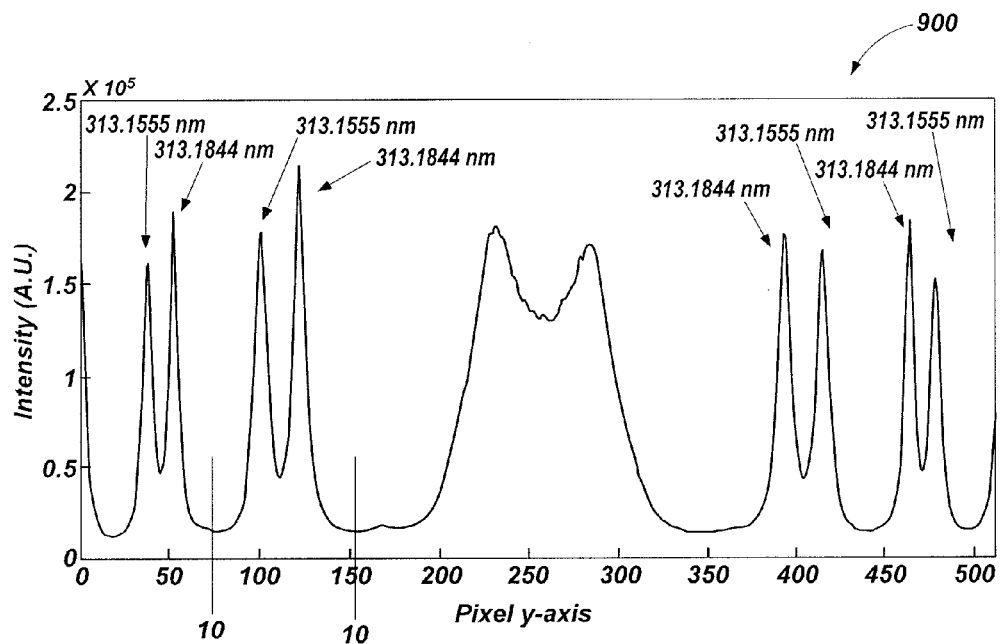
Figure 10:
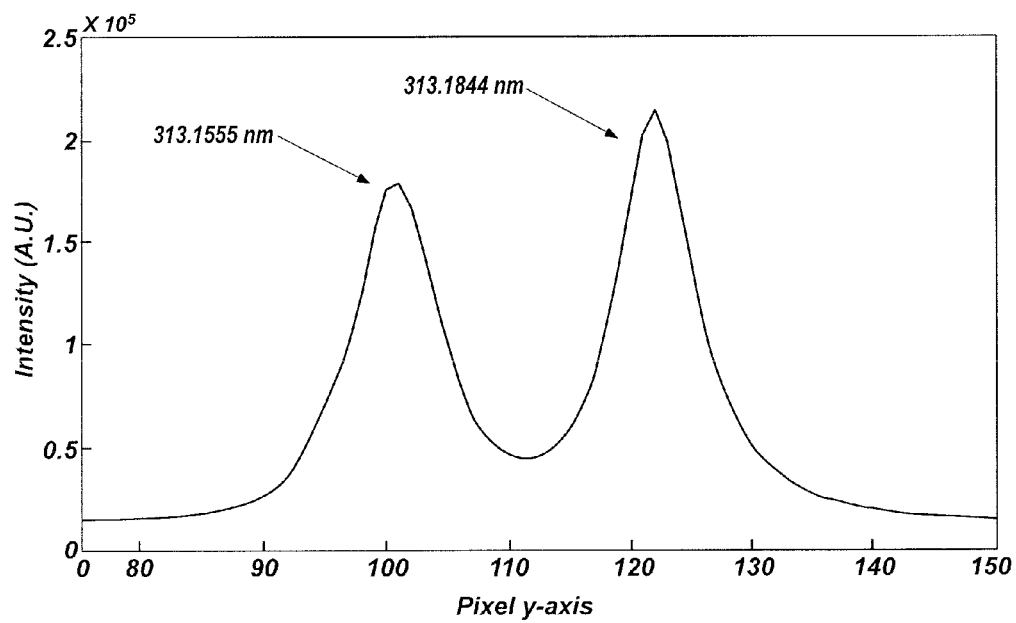

FIGS. 8 through 10 show analysis of the final images generated by the LIBS system 100 of FIG. 1. For demonstration and purposes of comparison, the final images of FIGS. 8 through 10 are the result of the LIBS system 100 having a continuous light source (e.g., Hg lamp) passing through the constructive interference object 130 and the dispersion element 140, rather than having a pulsed laser source create a plasma 104 of the sample 102. Generating a continuous light source for most analytes generally takes time-consuming sample preparation and adds additional instrumentation to a system.

Figure 11:
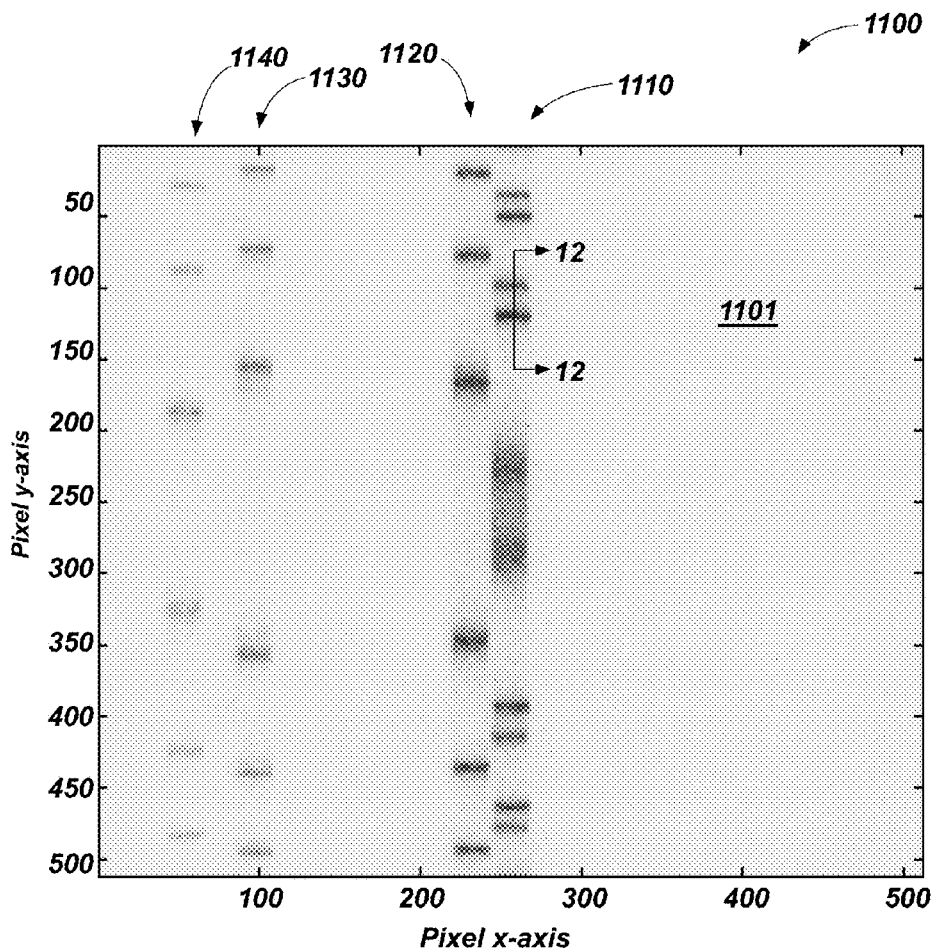
FIGS. 11 and 12 show analysis of the final images of the LIBS system of FIG. 1 using a pulsed laser source creating the plasma of the sample.
Figure 12:
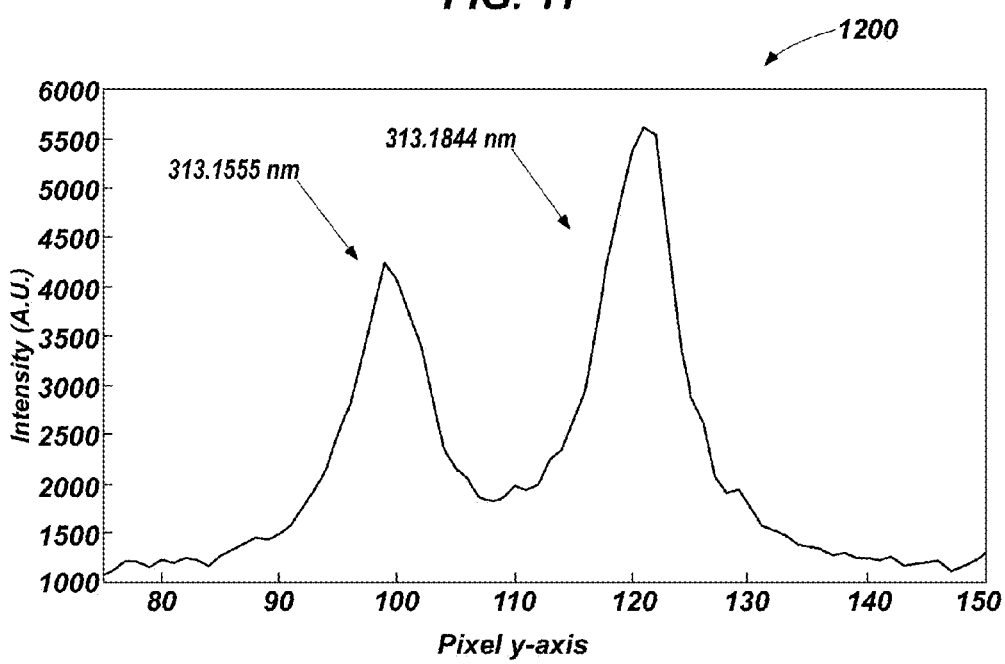

FIGS. 11 and 12 show analysis of the final images of the LIBS system 100 of FIG. 1 using a pulsed laser source creating the plasma 104 of the sample 102. The light associated with FIGS. 11 and 12 is from the laser generated plasma 104 of a cinnabar (HgS) sample. Of course, it is contemplated for other samples to be used depending on the desired sample for determining the material constituents and isotopic measurements thereof. Challenges of using the constructive interference object 130 and the dispersion element 140 with the low light levels and pulsed nature of LIBS are discussed below with reference to FIGS. 14 through 16.

Referring specifically to FIG. 8, FIG. 8 is a plot 800 of the strips of filtered rings of light output as the final image onto the image sensor 150, such as in the LIBS system of FIG. 1. For example, the x- and y-axes form a pixel area 801 of the image sensor 150. As discussed above with respect to FIGS. 1 and 2, the constructive interference object 130 may generate rings 132 of light responsive to the light 106. In addition, the dispersion element 140 may comprise a grating (e.g., 1800 g/mm), which may cause a sufficient dispersion of the rings 132 of light into columns along the pixel area 801. The dispersion element 140 may also limit a subset of wavelengths to be projected onto the pixel area 801 of the image sensor 150. For example, the projection of the final image onto the pixel area 801 may be an Hg emission, in which the 312.6 nm Hg line has been split from the 313.2 nm Hg line. Column 810 is the 313.2 nm line of the Hg emission, and column 820 is the 312.6 nm line of the Hg emission.

FIG. 9 is a plot 900 of the filtered rings 142 received by the image sensor 150. In particular, the plot 900 shows the summed intensities of the 313.2 nm line of the Hg emission along the line 9-9 of FIG. 8 (i.e., column 810). In other words, the y-axis of the pixel area 801 of FIG. 8 is along the horizontal axis of FIG. 9. The vertical axis of FIG. 9 is the intensity of the 313.2 nm line of the Hg emission of FIG. 8.

FIG. 10 is a zoomed-in, enlarged portion of the filtered rings 142 of the intensities of the 313.2 nm line of the Hg emission. In particular, FIG. 10 shows the portion of the 313.2 nm line of the Hg emission between lines 10-10 of FIG. 9. The Hg emission at 313.2 nm was used to evaluate instrument performance because the 313.2 nm doublet was chosen due to the similar hyperfine splitting (a splitting of 29 pm) as the isotope splitting of uranium at 424.437 nm (a splitting of 25 pm). For FIGS. 8 through 10 using a continuous light source, the Hg emission was resolved from a continuous source Hg lamp with a two second acquisition time.

FIG. 11 is a plot 1100 of the final image created from a LIBS system of FIG. 1 using a pulsed laser, as opposed to a continuous light source as was described with reference to FIGS. 8 through 11. For the results of FIG. 11, a cinnabar (HgS) sample was mounted on a sample holder in a vacuum chamber having a helium (He) atmosphere of 10 Torr. The pulsed laser operated for one minute with a laser pulse rate of 10 Hz, or a total of 600 accumulated laser pulses. The final image is projected onto a pixel area 1101 of the image sensor 150. The final image is the light 106 after being translated by the constructive interference object 130 and the dispersion element 140. The constructive interference object 130 generated rings 132 of light that are concentric having radii that are dependent on the wavelengths of the photons, and which are characteristic to the emissions from the material constituents of the sample 102. The dispersion element 140 generated vertical columns for the rings (i.e., filtered rings 142), and which are further separated into wavelengths. As with FIG. 8, the optical emission spectrum that is characteristic to Hg is separated into a column 1110 (i.e., 313.2 nm), and a column 1120 (i.e., 312.6 nm). FIG. 8, however, shows additional columns 1130, 1140 that are attributable to the characteristic optical emission spectrum of the sulfur (S) constituent of the cinnabar, which was not present in FIG. 8.

FIG. 12 is a zoomed-in, enlarged portion 1200 of the column 1110 of the intensities of the 313.2 nm line of the Hg emission of FIG. 11. In particular, the processing of the portion 1200 of the column 1110 of the 313.2 nm line is taken along line 12-12 of FIG. 11. As shown in FIG. 12, the LIBS system having a pulsed laser source and configured as discussed resolves the Hg doublet in a similar manner as using a continuous light source.

Figure 13:
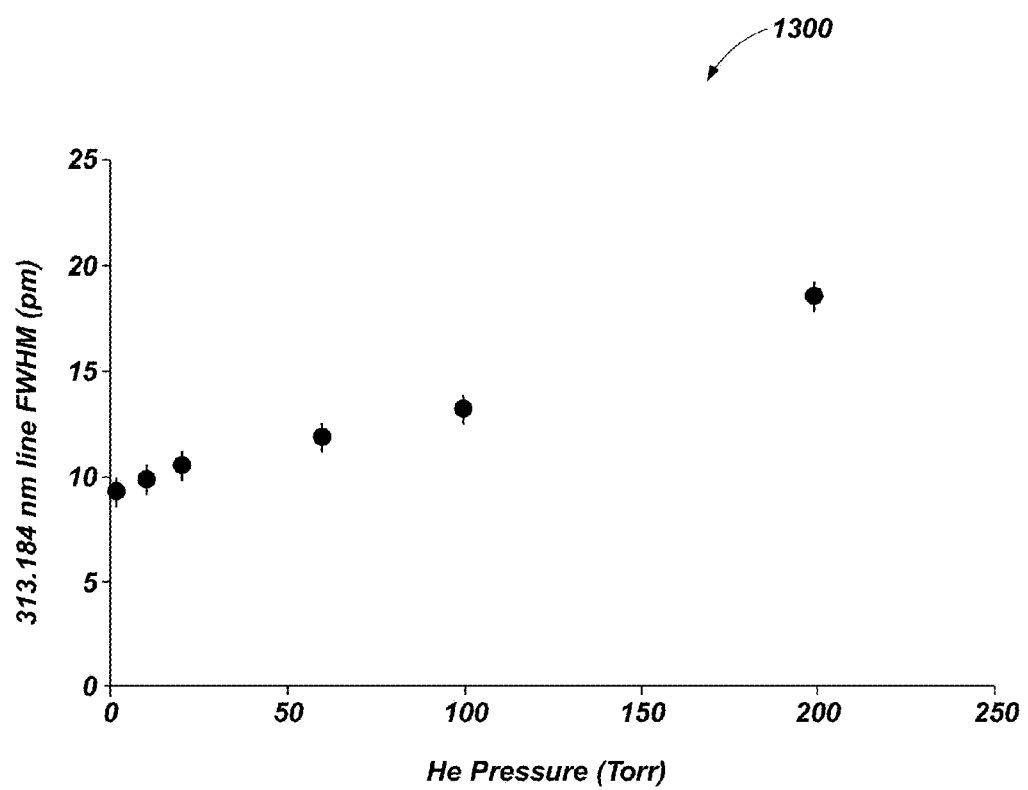
FIG. 13 is a plot of the FWHM for the 313.1844 nm doublet of the Hg emission in a He atmosphere at various pressures.

FIG. 13 is a plot 1300 of the FWHM for the 313.1844 nm doublet of the Hg emission in a He atmosphere at various pressures ranging from 10 Torr to 300 Torr. The 313.1844 nm line used in FIG. 13 was generated by a pulsed laser and LIBS being directed upon a cinnabar sample from the accumulation of 600 laser pulses at rate of 10 Hz (i.e., for one minute). As shown in FIG. 13, the LIBS system if configured and operated according to the present disclosure, produces results that are highly comparative (e.g., FWHM in the range of 10 pm for most pressures shown) with conventional LIBS systems that operate with Czerny-Turner spectrometers having relatively long focal length (e.g., 2 m). As a result, a smaller, more compact LIBS system may be implemented while maintaining an appropriate resolution and resolving power.

The use of other atmospheres and pressures within the chamber are contemplated, in addition to those shown in FIG. 13. A He atmosphere has a high ionization potential (24.4 eV) and high thermal conductivity compared with other gases, such as $N_2$ or Ar. The high ionization potential and thermal conductivity of He may result in a reduction of Stark broadening and pressure broadening. Different pressures may be desirable for resolving certain isotopes. For example, a He atmosphere of 100 Torr may provide desirable conditions for resolving Pu isotopes, while 10 Torr may be desirable for resolving the Hg doublet. The desired atmospheric conditions may further vary depending on other experimental variables, such as the way the plasma is viewed and the gating of the image sensor.

Referring again briefly to FIG. 1, the LIBS system 100 detects the light 106 that is generated by a plasma 104 being created by a laser pulse 112 rather than a continuous light source. In addition, passing the light 106 through the constructive interference object 130 (e.g., Fabry-Perot etalon) may reject a significant amount of light from the light 106. For example, as much as 99% of the light 106 may be rejected by the constructive interference object 130 that has a relatively high Feff. As a result, relatively low light levels may be detected by the image sensor 150. In addition, as the spectra intensity may be lower, noise may be more apparent. In other words, the signal-to-noise ratio (S/N) of the final image detected by the image sensor 150 may be relatively low.

One method for improving S/N of the final image is to widen the slit 241 (FIG. 2) in order to allow more light to be collected; however, doing so may also cause the rings in the final image to express curvature when projected onto the image sensor 150. Such curvature may not easily be added from the bins of the image sensor 150. Therefore, improving the S/N of the final image received by the image sensor 150 may be achieved by converting the curved light patterns into an appropriate spectrum.

Figure 14:
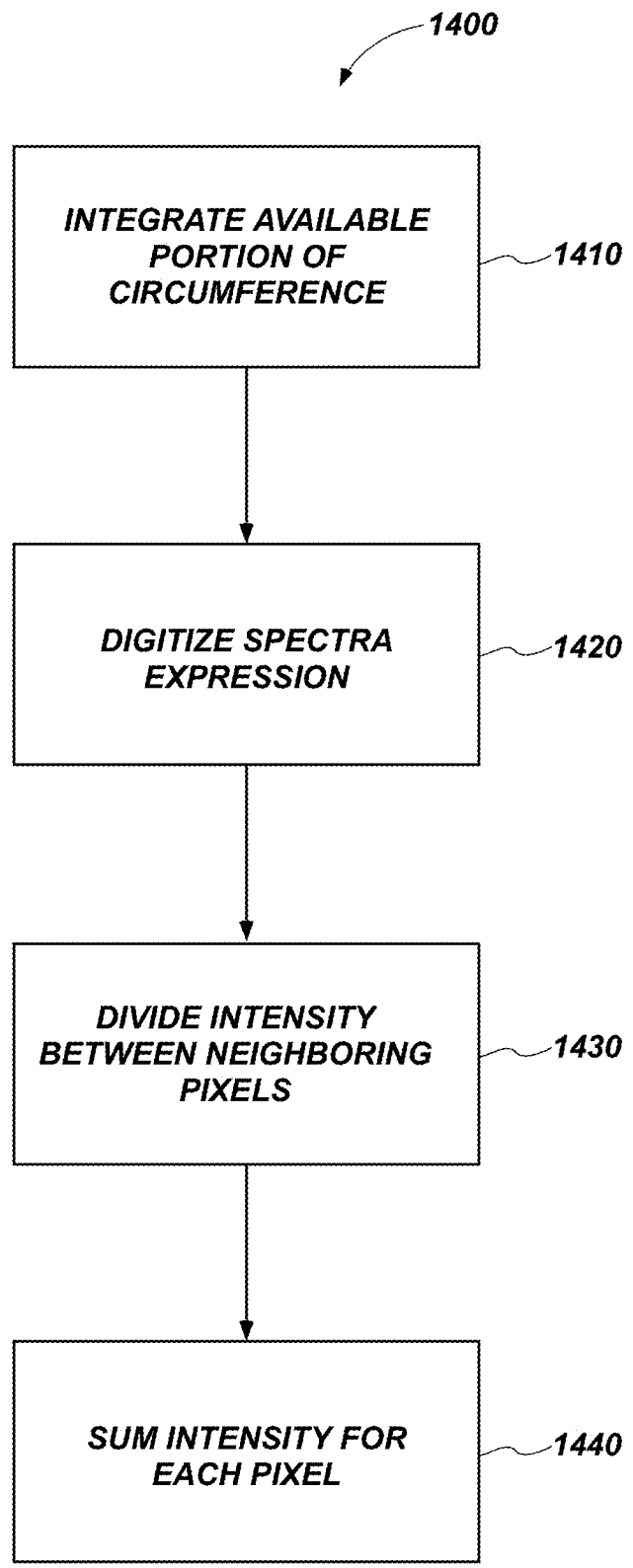
FIG. 14 is a flow chart illustrating a method for improving the signal-to-noise ratio of a final image of a LIBS system according to an embodiment of the present disclosure.

FIG. 14 is a flow chart 1400 illustrating a method for improving S/N of a final image of a LIBS system according to an embodiment of the present disclosure. Because the photons are distributed over the entire circumference of each ring of the final image, a higher relative magnitude accuracy may be obtained if the band is integrated over the available field. Because the application dispersion element 140 uses a slit 241, only a portion of the circumference of each ring is available. As a result, the integral may be set to integrate over the portion of the band that is available and then may be normalized based on the portion of the circumference that is available.

Figure 15:
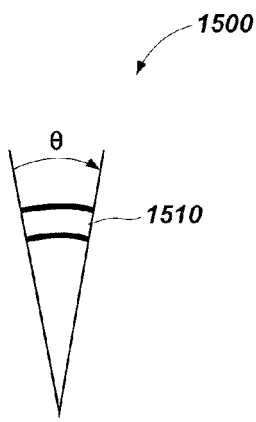
FIG. 15 depicts a region of a portion of a ring of the final image, for which curved light patterns are converted into a spectrum to improve signal-to-noise ratio of the final image.

At operation 1410, the available portion of the circumference of the rings may be integrated. As an example, FIG. 15 depicts a region 1500 of a portion of a ring of the final image, for which curved light patterns 1510 are converted into a spectrum to improve S/N of the final image. In other words, FIG. 15 shows the region 1500 over which the image can be integrated to count the photons over the entire circumference of the arc segment that is available.

For a continuous image, the integral equation to generate a spectrum over the arc is expressed in the numerator of:

$$s(r) = \frac{\int_{\theta 1(r)}^{\theta 2(r)} I(r, \theta) d\theta}{\theta 2(r) - \theta 1(r)}, \quad \text{Eq. (1)}$$

where $I(r,\theta)$ is the intensity of the image at the polar coordinates $(r,\theta)$ from the center of the final image. The starting and ending points for the integral vary with r because of the grating separates the image into rectangular "bands" (i.e., columns). The denominator of equation (1) normalizes for the variable "r" by dividing by the arc length of the integration. As shown in FIG. 11, the bands diametrically opposed to each other are part of the same circular band and can optionally be added into the spectrum.

As the final image may be a digital array created from an image sensor 150 (FIG. 1) on a rectangular pixel array, a method for interpolating each pixel to the appropriate point on the discrete spectrum may be defined. At operation 1420, the spectra expression will be digitized in a like manner as a set of intensities, such as:

$$s(i) = \{s(0\Delta R), s(\Delta R), s(2\Delta R), \ldots s(i\Delta R) \ldots s(N\Delta R)\} \quad \text{Eq. (2)},$$

where $\Delta R$ is a desired resolution, which may be no smaller than the minimum spacing between image pixels of the image sensor, as each pixel in the band has a radius from the center of the image pattern. For all but the case of the pixels on the vertical cross-section the pixel radius will fall between the sample points in the set of intensities $s(i)$.

At operation 1430, the intensity may be divided between neighboring pixels, such as by interpolation. For example, the intensity (I) of a point (j,k) has a radius of:

$$r(j,k) = \Delta R \sqrt{(j-Cj)^2 + (k-Ck)^2} \quad \text{Eq. (3)},$$

where j is the column pixel number and k is the row pixel number and Cj and Ck are the center of the image. If two sample radii are identified that are closest to the radius for this pixel, the radius immediately smaller than $r(j,k)$ may be assigned the intensity:

$$\hat{I}(p\Delta R) = \hat{I}(j,k)(\Delta R - r(j,k) + p\Delta R)/\Delta R \quad \text{Eq. (4)},$$

wherein "p" is the index of the radial position in the mapping from the image to the spectra. The next radius may be assigned the remainder intensity:

$$\hat{I}((p+1)\Delta R) = \hat{I}(j,k) - \hat{I}(p\Delta R), \quad \text{Eq. (5)},$$

and $I(p)$ may be assigned 0 intensity for all other points.

At operation 1440, each pixel may be processed in the valid region and the intensity divided for each pixel is summed for the appropriate samples in $s(i)$ to arrive at the spectrum having an intensity with an increased available S/N extracted from the image:

$$s(p) = \frac{\sum_{p,k} \hat{I}(p, j, k)}{\theta 2(p) - \theta 1(p)}, \quad \text{Eq. (6)}$$

where (p, j, k) is the intensity from a pixel intensity $I(p, j, k)$ attributed to the radial intensity p based on the equations above for interpolating pixel between discrete radii (i.e., operation 1430). In equation (6), "p" is the index of the radial position in the mapping from the image to the spectra, while "j" and "k" are the pixel positions. The intensity (I) may be equal to an intensity of 0 for all but the two nearest discrete radii. The summation of operation 1440 may be normalized over the valid arc segment for the radius of the rings of the final image.

Figure 16:
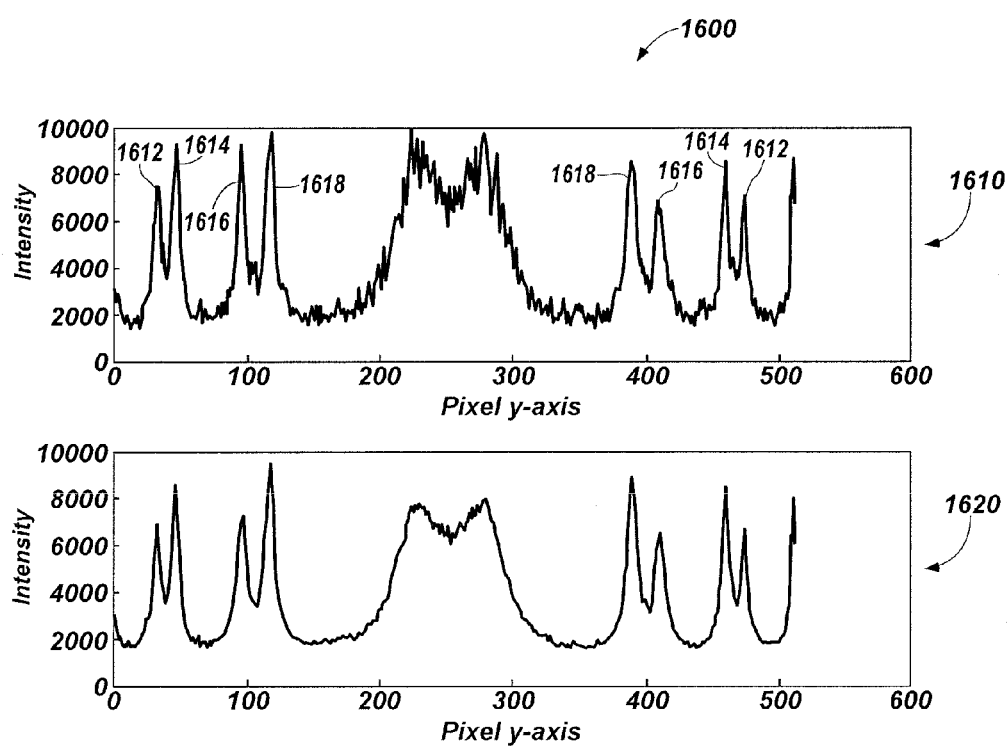
FIG. 16 depicts a plurality of cross sections of the summed intensities with and without the signal-to-noise ratio improvements described in the method of FIG. 14.

FIG. 16 depicts a plurality of cross sections 1600 of the summed intensities with and without the S/N improvements described in the method of FIG. 14. For example, the intensities of plot 1610 does not show an improvement to the S/N, whereas plot 1620 does show an improvement to the S/N having had the method described in FIG. 14 applied thereto. In some embodiments the S/N may be further improved by merging the outer doublet rings with their respective inner doublet rings, as the outer doublet rings are repetitions from the inner doublet rings. In other words, outer doublet rings 1612 may be merged with inner doublet rings 1616, and outer doublet rings 1614 may be merged with inner doublet rings 1618.

LIBS systems and related optical systems of the present disclosure may be implemented in a wide range of industries and measurement applications for various isotopes (e.g., C, H, N, O, S stable isotopes). For example, contemplated applications include material analysis, radiological quality control, nuclear nonproliferation and safeguard monitoring, geochronology, forensics, environmental monitoring, biological identification, mining exploration and processing, petroleum industry, forensics, and in the analysis of artworks.

As a few specific examples, nuclear energy may employ isotope signatures to monitor fuel burn-up rates and efficiency of fuel processing or reprocessing. Additionally, isotope signatures can be used for nuclear nonproliferation monitoring to determine if nuclear fuel is being processed according to treaty agreements (i.e., illicit diversions of nuclear material are not occurring). Geochronology, archeology, and some environmental monitoring may use isotope signatures, such as by determining Rb-87/Sr-87 for dating rocks. Conventional methods for dating rocks have relied on acquiring samples in the field and taking the samples back to a laboratory for extensive sample preparation and analysis, which may take months to obtain the results. Even after obtaining the results, a subsequent trip to the field site is often required. A portable high-resolution LIBS system may be beneficial in allowing the data to be acquired in real time during the initial field trip, enabling decisions (e.g., where to take other samples) to be made on location.

Isotopes may also be used by the food and perfume industries to assess adulteration of edible and essential oils, respectively. Drug testing also uses these types of isotopes to distinguish between natural and synthetic testosterone. There is interest in small, high performance instruments for monitoring isotopes for signs of life and various isotopes for geochronology for space exploration applications. Forensics is another discipline that is turning more and more toward isotope data, as opposed to element only data, for identifying source materials or tracking the origin and movements of people (e.g., isoscapes). For example, bullets can be fingerprinted by the ratio of lead isotopes. Information that may be desired in the monitoring of nuclear processing and forensics are the isotope ratios of special nuclear material. The petroleum industry uses sulfur and carbon isotopes to identify sources. Isotope data is not only used in field exploration, but also to assess oil clean-up efforts. In addition, the isotope data may be used to monitor the change in oils moving in pipelines.

In addition, while examples of applications have been given that relate to the detection of isotopes, it is contemplated that the embodiments of the present disclosure may also be used for hyperfine structure applications as would be understood by those skilled in the art. As embodiments of the present disclosure may contribute to a relatively smaller design that may result in a more portable apparatus with a relatively high resolution, many additional applications may benefit from an increased ability to perform the measurements in the field or at the site (in situ), and in real-time.

CONCLUSION

An embodiment of the present disclosure includes an apparatus. The apparatus comprises a pulsed laser configured to generate a pulsed laser signal toward a sample, a constructive interference object and an optical element, each located in a path of light generated by the sample. The constructive interference object is configured to generate constructive interference patterns of the light. The optical element is configured to disperse the light.

Another embodiment of the present disclosure includes a laser-induced breakdown spectroscopy system. The laser-induced breakdown spectroscopy system comprises a chamber configured to house a sample, a pulsed laser configured to generate a laser pulse into the chamber onto the sample to create a plasma generating light, and an image sensor. The laser-induced breakdown spectroscopy system further comprises a first optical element and a second optical element, and a data acquisition module. The first optical element is configured to receive the light and generate a plurality of concentric rings having a radius that is dependent on at least one wavelength of the light. The second optical element is configured to receive the light and disperse the light onto the image sensor. The data acquisition module is operably coupled with the image sensor, and is configured to determine an isotope measurement based, at least in part, on the light received by the image sensor.

Yet another embodiment of the present disclosure includes a method for performing laser-induced breakdown spectroscopy. The method comprises generating a pulsed laser on a sample to generate light from a plasma, generating constructive interference patterns of the light, and dispersing the light into a plurality of wavelengths.

While the invention is susceptible to various modifications and implementation in alternative forms, specific embodiments have been shown by way of non-limiting examples in the drawings and have been described in detail herein. However, it should be understood that the invention is not intended to be limited to the particular forms disclosed. Rather, the invention includes all modifications, equivalents, and alternatives falling within the scope of the following appended claims and their legal equivalents.

What is claimed is:

1. A laser-induced breakdown spectroscopy apparatus, comprising:
   a pulsed laser configured and oriented to generate a pulsed laser signal toward a sample;
   a constructive interference object located in a path of light of a plasma generated by the sample responsive to the pulsed laser signal, and configured to generate constructive interference patterns of the light;
   an optical element located in the path of the light serially with the constructive interference object, the optical element configured to disperse the light; and
   a gated image sensor including a two-dimensional array configured to receive the light from the constructive interference object and the optical element, and generate a digital image of the received light.

2. The laser-induced breakdown spectroscopy apparatus of claim 1, wherein the constructive interference object is a Fabry-Perot etalon.

3. The laser-induced breakdown spectroscopy apparatus of claim 1, wherein the optical element is a dispersion element configured to disperse the light into columns.

4. The laser-induced breakdown spectroscopy apparatus of claim 3, wherein the dispersion element is a Czerny-Turner spectrometer.

5. The laser-induced breakdown spectroscopy apparatus of claim 1, wherein the optical element is a second constructive interference object.

6. The laser-induced breakdown spectroscopy apparatus of claim 1, wherein the optical element is positioned to receive the light exiting the constructive interference object.

7. The laser-induced breakdown spectroscopy apparatus of claim 1, further comprising a fiber optic cable configured to receive the light from the sample and transmit the light to the constructive interference object and the optical element.

8. The laser-induced breakdown spectroscopy apparatus of claim 7, wherein the fiber optic cable comprises the constructive interference object and the optical element.

9. The laser-induced breakdown spectroscopy apparatus of claim 1, wherein the gated image sensor is selected from the group consisting of a charge-coupled device and a CMOS imager.

10. The laser-induced breakdown spectroscopy apparatus of claim 1, further including a data acquisition module operably coupled with the gated image sensor and configured to analyze the digital image and generate a spectrum in response thereto.

11. The laser-induced breakdown spectroscopy apparatus of claim 10, further comprising a chamber configured to house the sample.

12. The laser-induced breakdown spectroscopy apparatus of claim 11, wherein the chamber is selected from the group consisting of a vacuum chamber and an atmospheric chamber.

13. The laser-induced breakdown spectroscopy apparatus of claim 10, wherein the data acquisition module is further configured to convert curved light patterns of the digital image into a spectrum for a plurality of neighboring pixels of the gated image sensor.

14. A laser-induced breakdown spectroscopy system, comprising:
   a chamber configured to house a sample;
   a laser configured to generate a laser pulse onto the sample within the chamber to create a plasma generating light;
   a gated image sensor including a two-dimensional array configured to generate a digital image of the light;
   a first optical element configured to receive the light and generate a plurality of concentric rings having a radius dependent on at least one wavelength of the light;
   a second optical element serially located with the first optical element, and configured to receive the light and disperse the light onto the gated image sensor; and
   a data acquisition module operably coupled with the gated image sensor, and configured to determine an isotope measurement based, at least in part, on the light received by the gated image sensor.

15. The laser-induced breakdown spectroscopy system of claim 14, wherein the laser is a Nd:YAG pulsed laser.

16. The laser-induced breakdown spectroscopy system of claim 14, wherein the first optical element is selected from the group consisting of an etalons and an interferometer.

17. The laser-induced breakdown spectroscopy system of claim 14, wherein the second optical element is selected from the group consisting of a spectrometer, a prism, and an optical fiber.

18. The laser-induced breakdown spectroscopy system of claim 14, wherein the second optical element comprises a Czerny-Turner spectrometer having a diffraction grating.

19. The laser-induced breakdown spectroscopy system of claim 18, wherein the Czerny-Turner spectrometer has a focal length of approximately 0.5 meter or less.

20. A method for performing laser-induced breakdown spectroscopy, comprising:
   generating a pulsed laser on a sample to generate light from a plasma;
   generating constructive interference patterns of the light;
   dispersing the light into a plurality of wavelengths, wherein generating the constructive interference patterns and dispersing the light occur through optical elements that are located in a serial path of the light from the plasma; and
   generating a digital image responsive to collecting, with a two-dimensional gated image sensor, the dispersed light that has passed through the optical elements.

21. The method of claim 20, wherein dispersing the light includes dispersing the constructive interference patterns of the light.

22. The method of claim 20, further comprising converting curved light patterns of the digital image into a spectrum for a plurality of neighboring pixels of the two-dimensional gated image sensor that receives the dispersed light.

23. The method of claim 22, wherein converting curved light patterns of a digital image into a spectrum includes:
   integrating an available portion of the curved light patterns received by the two-dimensional gated image sensor;
   digitizing a spectral expression of the curved light patterns as a set of intensities;
   dividing at least one intensity of the set of intensities between the neighboring pixels of the two-dimensional gated image sensor; and
   summing a plurality of intensities for each of the neighboring pixels to obtain an intensity for each individual one of the neighboring pixels.

24. The method of claim 20, further comprising determining an isotope based, at least in part, on a characteristic photon wavelength detected in the plurality of wavelengths and associated with the sample.

25. The method of claim 20, wherein generating constructive interference patterns of the light includes generating rings of the light that have a radius that corresponds to a characteristic photon wavelength.

26. The method of claim 25, wherein dispersing the light includes dispersing the rings of the light into columns according to the characteristic photon wavelength.

* * * * *